United States Patent [19]
Offord

[11] Patent Number: 5,770,447
[45] Date of Patent: Jun. 23, 1998

[54] CELL LINE FOR THE RAPID EXPRESSION OF FUNCTIONAL CALCIUM CHANNELS

[75] Inventor: James David Offord, Ann Arbor, Mich.

[73] Assignee: Warner-Lambert Company, Morris Plains, N.J.

[21] Appl. No.: 923,489

[22] Filed: Sep. 4, 1997

Related U.S. Application Data

[62] Division of Ser. No. 467,203, Jun. 6, 1995, Pat. No. 5,712,158.

[51] Int. Cl.⁶ ............................... C12N 5/00; C12N 15/00
[52] U.S. Cl. .......................... 435/369; 435/172.1; 935/59
[58] Field of Search ................................. 435/369, 172.1; 935/59

[56] References Cited

U.S. PATENT DOCUMENTS

| | | | |
|---|---|---|---|
| 5,386,025 | 1/1995 | Jay et al. | 536/23.5 |
| 5,429,921 | 7/1995 | Harpold et al. | 435/4 |

FOREIGN PATENT DOCUMENTS

| | | |
|---|---|---|
| 0 556 651 | 8/1993 | European Pat. Off. . |
| 93/04083 | 3/1993 | WIPO . |
| 95/04822 | 2/1995 | WIPO . |
| 96/03122 | 2/1996 | WIPO . |

OTHER PUBLICATIONS

Gee et al. (1996) J. Biol. Chem. 271(10): 5768–5776.
PCT International Search Report, PCT/US 96/08835.
Derwent Abstract AN 96–110269, Eisai Co. Ltd.
Welling et al. (1993) J. Physiol. 471: 749–765.
Brust et al. (1993) Neuropharmacology 32(11): 1089–1092.
Williams et al. (1992) Science 257: 389–395.
Heinemann et al. (1992) Nature 356:441–443.
Kim et al. (1993) FEBS Letts. 318(2):145–148.
Bleakman et al. (1995) Neuropharmacology 34(7):753–765.
Williams et al. (1994) J. Biol. Chem. 269(35):22347–22357.

*Primary Examiner*—Robert A. Wax
*Assistant Examiner*—Lisa J. Hobbs
*Attorney, Agent, or Firm*—Elizabeth M. Anderson

[57] ABSTRACT

The instant invention provides a stable cell line, 34893 2L, for the rapid functional expression of high voltage activated calcium channels.

1 Claim, 6 Drawing Sheets

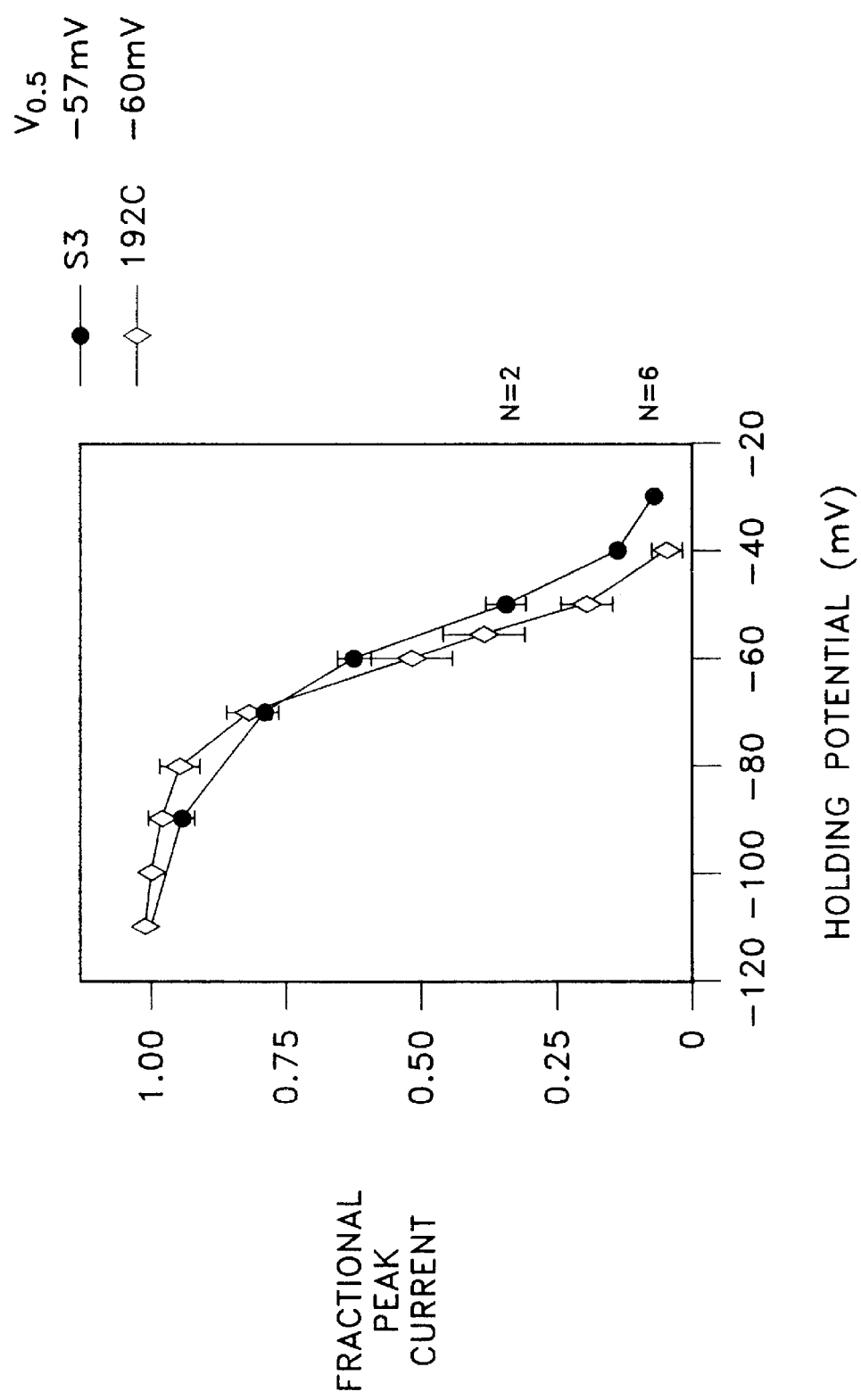

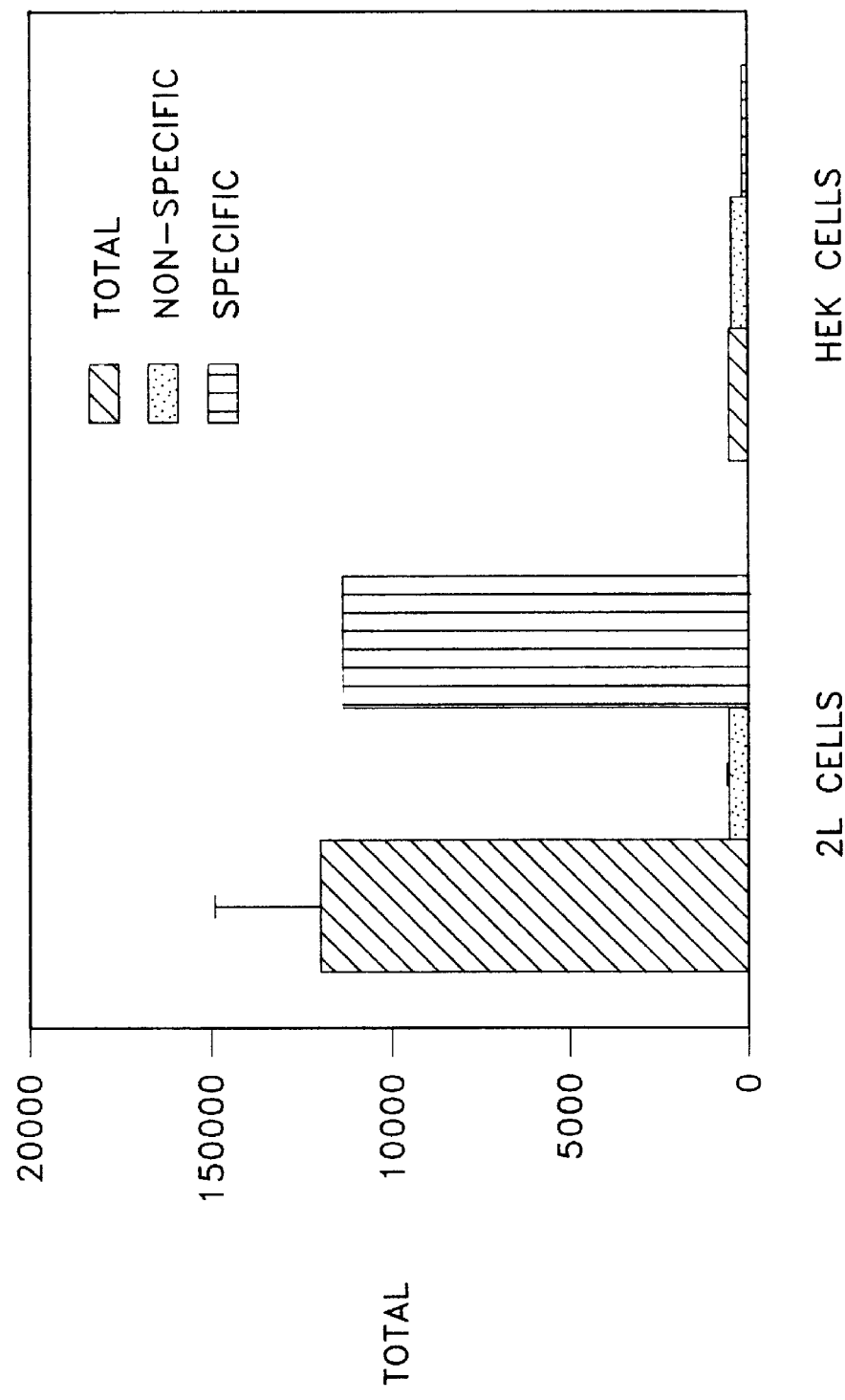

CELL LINE FOR THE RAPID EXPRESSION OF FUNCTIONAL CALCIUM CHANNELS

This application is a division of application Ser. No. 08/467,203 filed Jun. 6, 1995 which application is now U.S. Pat. No. 5,712,158.

BACKGROUND OF THE INVENTION

The voltage activated calcium channels of vertebrates have been shown to be involved in a variety of different physiological processes including muscle contraction, insulin release from the pancreas, and neurotransmitter release in the nervous system (Catterall W. A., *Trends in Neurosciences*, 1993;16:500–506; Catterall W., Epstein P. N., *Diabetologia*, 35(Suppl 2:S23–33) 1992; Birnbaumer L., et al., *Neuron.*, 1994:13; Rorsman P., et al., *Diabete. Metab.*, 1994;20:138–145). The original description of the calcium channels classed them as T type, L type, or N type. The T type channel is activated at relatively low voltages, while the L and N types are activated by depolarization to higher voltages. The L type is a channel that is involved in muscle contraction, and is characterized by slow inactivation and sensitivity to dihydropyridines. The N type is also a high voltage activated channel, but rather than being sensitive to dihydropyridines, the N channel is blocked by the peptide toxins GVIa and MVIIA from cone snails, and is involved in neurotransmitter release (Birnbaumer L., et al., *Neuron.*, 1994:13; Olivera B. M., Miljanich G. P., Ramachandran J., Adams M. E., *Annu Rev. Biochem.*, 1994;63:823–867).

The channels purified from neural tissue and skeletal muscle contain a number of different subunits. The L channel from skeletal muscle consists of a complex containing five subunits, alpha 1, alpha 2, beta, delta, and gamma. L channels isolated from neuronal tissue consist of three subunits corresponding to the alpha 1, alpha 2, and beta subunits. Delta and gamma do not seem to be expressed in the nervous system (Catterall W. A., *Trends in Neurosciences*, 1993;16:500–506).

The N type channel is expressed primarily in neuronal tissue, though there have been some reports of the channel being expressed in beta cells of the pancreas. The N channel is also made up of alpha 1, alpha 2, and beta subunits.

Recent experiments have shown that there are a number of other calcium channels in the central nervous system. The P type channel has been described in cerebellar Purkinje cells. This channel is a high voltage activated channel, but it differs from the N and L types primarily in its insensitivity to either dihydropyridines or cenotoxins. Instead, this channel is sensitive to the peptide toxin Aga IVa from the funnel web spider. Cerebellar granule cells express a high voltage activated channel that has been called R or Q and is insensitive to Aga IVa, the conotoxins MVIIA and GVIA, and dihydropyridines. It is sensitive to the conotoxin MVIIC (Birnbaumer L., et al., *Neuron.*, 1994:13).

Molecular cloning of the channel subunits from skeletal muscle and brain have revealed a significant similarity between the various different calcium channel subtypes. The level of conservation between the alpha 1 subunits of the N and L types is quite high, and this subunit has been identified as the subunit through which calcium ions flow. Several isoforms of alpha 2 and beta subunit clones have also been isolated from neuronal and muscle tissue, though there has been no definite assignment of specific isoforms to a particular type of calcium channel. As yet, there is no definite assignment of the P/Q type to a cloned cDNA.

Expression experiments in *Xenopus oocytes* have demonstrated that in order to produce fully functional calcium channels, the alpha 1, alpha 2, and beta subunits must all be expressed. Absence of either the alpha 2 or beta subunit results in a nonfunctional channel, even though the alpha 1 subunit, through which ions flow, is fully expressed. Indeed, not only the ion flux through these channels but the pharmacological properties of the alpha 1 are different in the absence of the alpha 2 and beta subunits. Expression of an alpha 1 subunit with different beta subunits results in channels with different inactivation properties, indicating that the beta-alpha 1 interaction is important in regulating the functional properties of the channels.

Expression of calcium channels in mammalian cells has lagged behind expression in *Xenopus oocytes* in part because *Xenopus oocyte* expression is quite convenient and in part because stable expression in mammalian cells has proven difficult. Many properties of the channels can be analyzed by electrophysiological techniques in *Xenopus oocytes*, and some pharmacology can be done using this system. Mammalian expression would allow a better characterization of the binding properties of drugs and peptides. Yet it has proven difficult to generate stable cell lines; whether because of an intrinsic toxicity of the expressed channel, or the combinatorial problem of expressing three subunits simultaneously in a single cell. Indeed, some authors have speculated that it is not possible to generate a set of cells which are stably expressing calcium channels at high levels. (Brust P. F., et al., *Neuropharmacology*, 1993;32).

Transient expression has been obtained by a number of different groups. While these systems have allowed some further pharmacological characterization of the expressed channels, they are difficult to carefully reproduce from time to time, and depend on each of three different subunits being expressed in the same cells (Brust P. F., et al., *Neuropharmacology*, 1993;32; Williams M. E., et al., J. Biol. Chem., 1994;269:22347–22357).

One utility of cells expressing the alpha 2 and beta subunits of the calcium channel is in the area of transient expression. Recent work has identified regions of the calcium channel to which the conopeptides bind. These analyses were performed in Xenopus oocytes. In this system one can only measure the rates at which the peptides bind to the channel (Ellinor P. T., Zhang J. F., Horne W. A., Tsien R. W. *Nature*, 1994;372). Transient expression of these alpha 1 subunits in cells that are expressing the alpha 2 and beta subunits would allow for equilibrium binding measurements to be performed, allowing for more complete evaluation of the interaction between the channel and the peptides.

WO 95/04822 teaches isolated cDNAs encoding each of human calcium channel alpha 1 to alpha 2, beta, and gamma subunits, including subunits that arise as splice variants of primary transcripts. In particular, DNA clones encoding each of the alpha 1A-1, alpha 1A-2, alpha 1E-1, alpha 1C-2, alpha 1E-3, beta 3-1, beta 2C, beta 2D, beta 2E, and beta 4 subunits of human calcium channels are provided.

U.S. Pat. No. 5,386,025 teaches calcium channel gamma subunit encoding cDNAs.

The instant invention of developing stable cell lines expressing calcium channels by generating cells in which two of the subunits are expressed at high levels and using the 2L cells to transfect in the alpha subunit for any calcium channel to obtain cells expressing a new calcium channel type is not taught by the references.

SUMMARY OF THE INVENTION

The purpose of the instant invention is the development of cell lines that allow the rapid development of cell lines that are stably expressing a variety of different calcium channels.

The instant invention overcomes the difficulty in developing stable cell lines expressing calcium channels which is due in large part to obtaining stable incorporation of three different subunit clones in a single cell line. By generating cells in which two of the three subunits are expressed at high levels, generation of cell lines that express high levels of channels has been greatly simplified. Now, using the 2L cells, one can simply transfect in the alpha 1 subunit for any of the different calcium channels and have cells expressing a new calcium channel type.

The 34893 2L cells are useful for developing clonal cell lines expressing calcium channels.

The 34893 2L cells are for the general expression of high voltage activated calcium channels of a variety of types including but not limited to N type channels, R type channels, Q type channels, and cardiac Class C, L type channels.

The 34893 2L cell line has been deposited under the Budapest Treaty and has an ATCC No. of CRL-12108. The 34893 2L cell line was deposited at the American Type Culture Collection (ATCC), 12301 Parklawn Drive, Rockville, Md. 20852 USA on May 17, 1996. The 34893 2L cell line has the characteristics of a transfected eukaryotic cell strain (HEK293) that expresses the subunits α2/delta from rabbit skeletal muscle and β2 from human neuronal tissue. The 34893 2L cells are grown in the presence of the antibiotic 6418 at a concentration of 600 micrograms per ml.

BRIEF DESCRIPTION OF THE DRAWINGS

FIGS. 3 and 3A are a comparison of currents.

FIG. 4 is the utility of the 348932 L cells.

Figure 1:
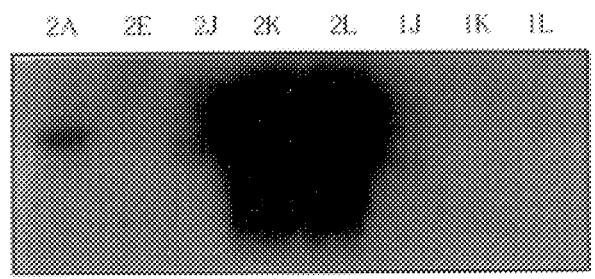
FIGS. 1 and 1A are a northern blot analysis of the RNA from several cell lines transfected with alpha 2 and beta subunit clones.
Figure 1A:
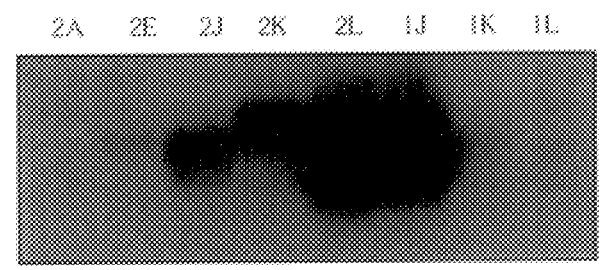

DETAILED DESCRIPTION
MATERIALS AND METHODS

Lipofectamine, RPMI 1640 medium, Optimem-1 medium, fetal bovine serum, and the antibiotic Geneticin were obtained from Life Technologies Inc.

HEK 293 cells were obtained from the American Type Culture Collection. The cells are maintained in RPMI 1640 medium supplemented with 2 mM glutamine and 10% fetal bovine serum.

The antibiotic Hygromycin B sulfate was obtained from Boehringer Mannheim. cDNAs for the rabbit skeletal muscle calcium channel alpha 2 subunit, and the human neuronal beta 2 subunit cloned into the expression vector pcDNAIII were obtained from Neurex. Human neuronal calcium channel alpha 1 subunits of E class and B class, cloned into the expression vector pcDNAIII, were obtained from Neurex.

HEK 293 cells were maintained in RPMI 1640 medium supplemented with 2 mM glutamine and 10% fetal bovine serum. One day prior to transfections, cells were trypsinized and counted. Cells were plated at a density of 300,000 to 500,000 cells per well in six well plates.

Cells were transfected using lipofectamine mediated transfection. Per well, 2 μg of neuronal beta-2 plasmid, and 2 μg of alpha 2 containing plasmid were mixed in 100 mL of optimem-1 medium. Twenty-five microliters of lipofectamine at a concentration of 2 mg/mL was added to a separate aliquot of optimem-1. The DNA containing medium and the lipofectamine containing medium was mixed and allowed to incubate at room temperature for 45 minutes. Eight hundred microliters of optimem-1 medium was added per 200 mL of lipofectamine-DNA mixture. Cells in six well plates were washed once with optimem-1, and then the DNA-lipofectamine mixture was layered onto the cells. The cells were incubated overnight at 37° C.

After overnight incubation, the cells were washed once with optimem-1 medium, then RPMI 1640 medium supplemented with 2 mM glutamine, and 10% fetal bovine serum was added to the cells. The cells remained in this nonselective medium for 2 days, then RPMI 1640 medium supplemented with 2 mM glutamine, and 10% fetal bovine, and also supplemented with Geneticin at a concentration of 600 μg/mL was added.

After 3 to 4 weeks of selection in this medium, cells which were resistant to G418 began to form colonies. Cloning cylinders were placed around the colonies, and the colonies were trypsinized. Each colony was then placed into separate wells of a 24 well plate and allowed to grow to confluence. After reaching confluence, each well was trypsinized, and transferred into two wells of a six well plate. After these wells reached confluence, each well was trypsinized, and one was frozen. The second well was used to seed two wells of a six well plate.

Cells in one of the duplicate wells were lysed in a guanidine thiocyanate solution and hybridized in solution with probes prepared from the alpha 2 and beta clones. Cell lines showing hybridization to either of these probes were expanded and RNA was prepared for northern blot analysis.

Cell lines that were expressing high levels of both alpha 2 and beta messenger RNA were expanded and used for subsequent transfections. The cells were maintained in selective medium. Transfections of the B class and E class alpha 1 subunits were accomplished essentially as above, but plasmid containing the gene for hygromycin resistance was co-transfected with the plasmids containing the cDNAs for the B and E class alpha 1 subunits. Selection was in medium containing G418 at a concentration of 600 μg/mL, and Hygromycin B sulfate at a concentration of 400 μg/mL. Cells were selected in this medium and characterized for expression of functional calcium channels by electrophysiological methods.

DETAILED DESCRIPTION OF THE DRAWINGS

FIG. 1 presents the results of the northern blot analysis of the RNA from several cell lines transfected with alpha 2 and beta subunit clones. It can be seen that the level of expression of these two subunits varies quite a bit from one transfected line to another. All of the cell lines showed positive for alpha 2 and beta in RNase protections, but each is expressing different amounts of the RNA.

The 2 L cell line is expressing the highest levels of both the alpha 2 and the beta subunit RNAs, and it was chosen as the vehicle for transfecting in B and E class alpha 1 clones.

Figure 2:
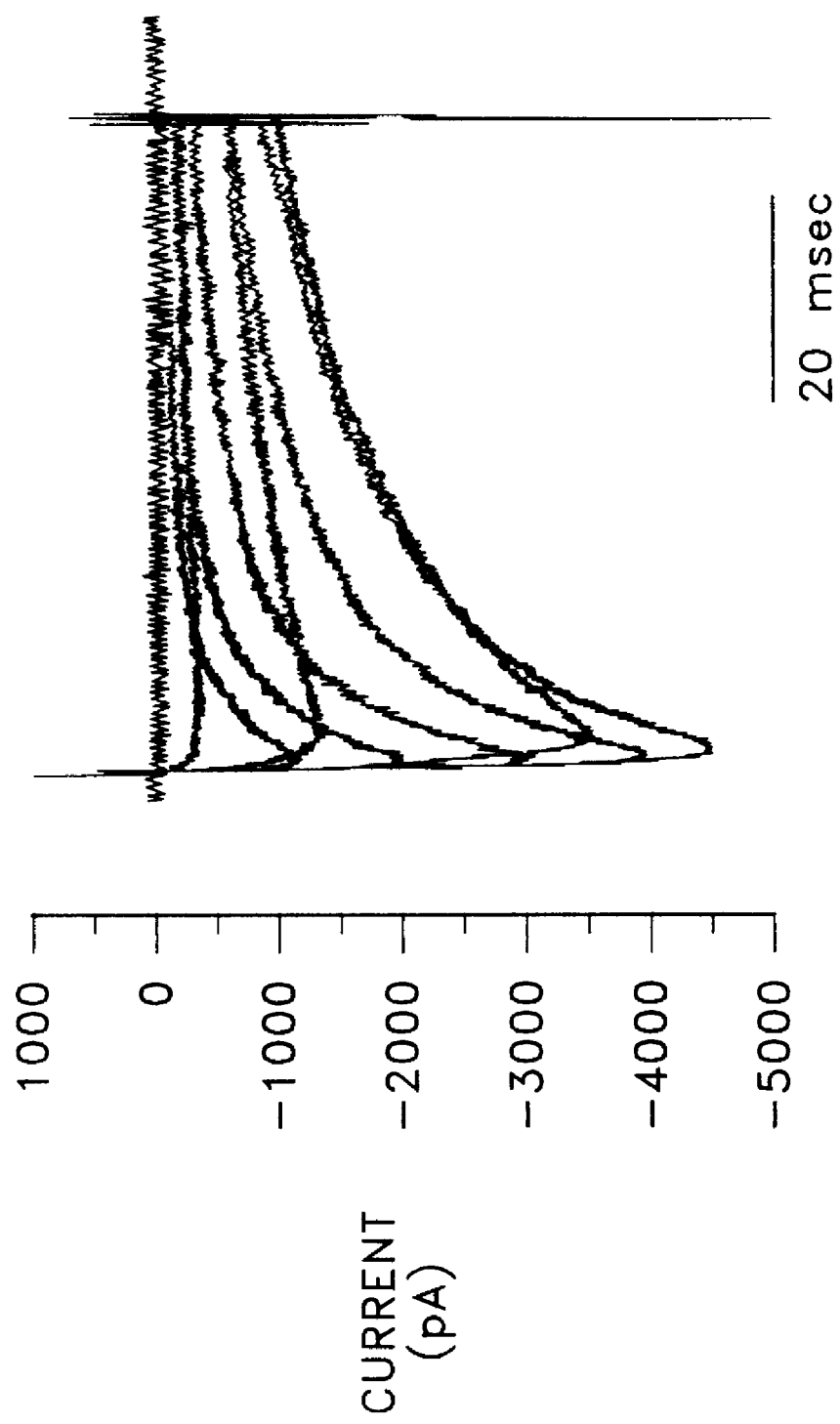
FIGS. 2 and 2A are electrophysiological analysis of the C class channel expressed in the two L cells.
Figure 2A:
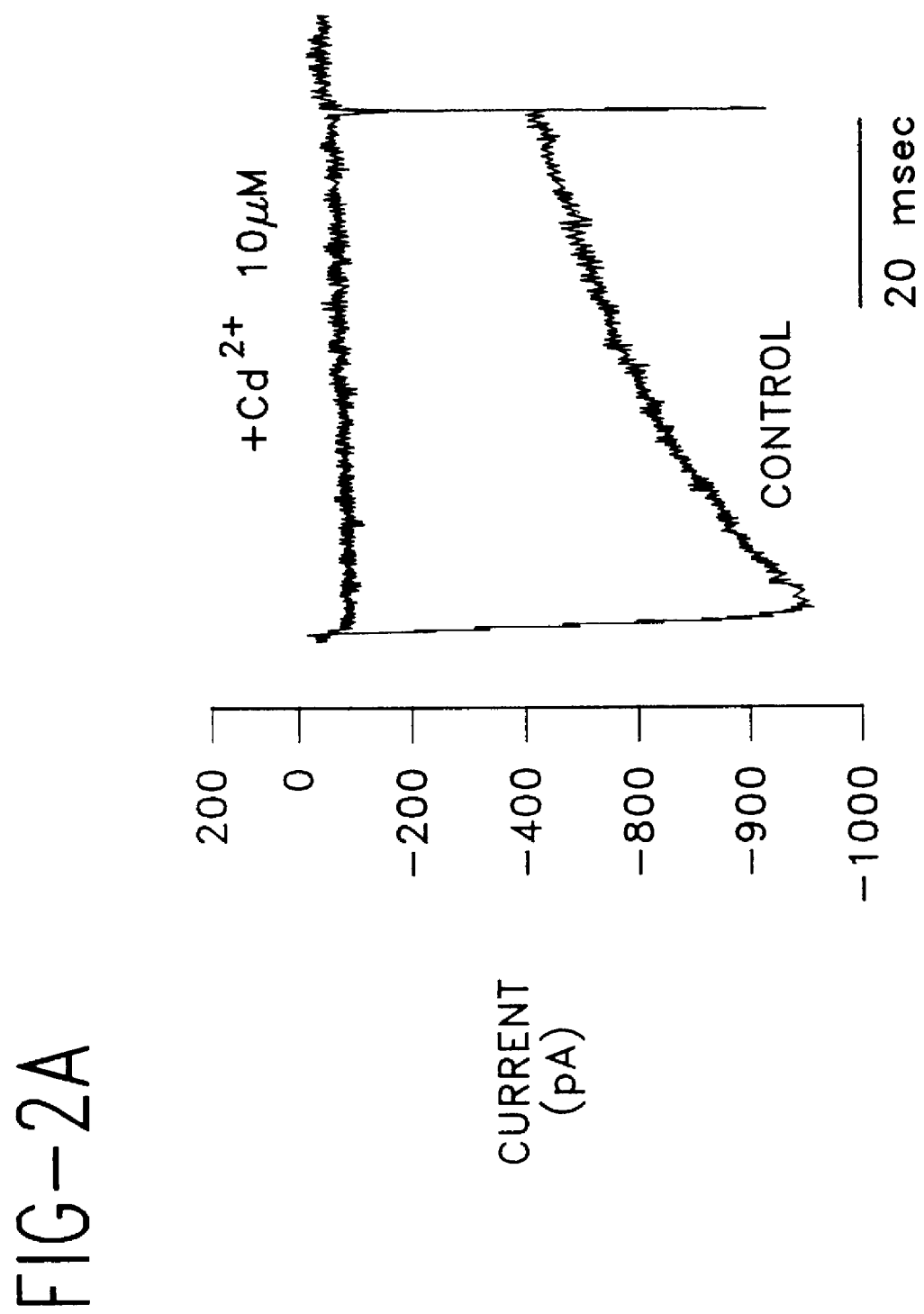

FIG. 2 presents the results of electrophysio-logical analysis of the E class channel expressed in the 2L cells. The channels expressed in these cells exhibits the standard electrophysiological properties of the E class channel. The channel is activated at high deplorizations (in this case a current step to 10 mV from a holding potential of −80 mV), the inactivation is relatively slow, and the channel is blocked by 10 μM $Cd^{2+}$.

Figure 3:
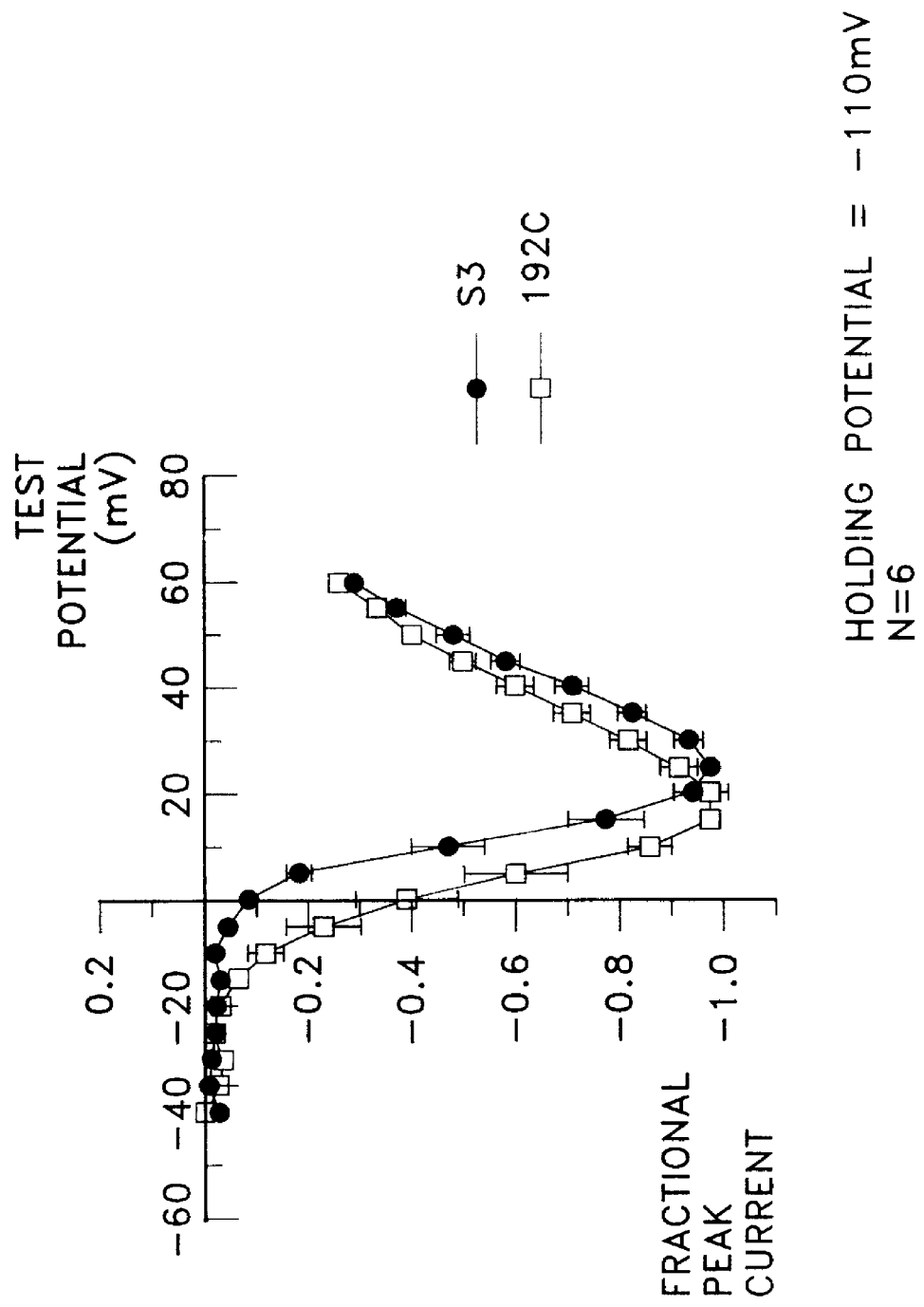

FIG. 3 shows a comparison of the currents from S3 cells (2L cells which have been transfected with the B class, or N type alpha 1) and 192C cells(2L cells transfected with the E class alpha 1). As can be seen, the cells express channels that are similar, but differ slightly in their activation kinetics, and inactivation kinetics.

FIG. 4 illustrates the utility of the 348932L cells in looking at the binding of Neurontin to the alpha 2 subunit of the calcium channel. The level of specific binding to the transfected cells is about 20 times higher than that seen in the parent, untransfected HEK 293 cells.

This therefore demonstrates the utility of 34893 2L cells for analyzing the binding of Neurontin (trademark for gabapentin) and the like compounds in competitive ligand binding assays.

I claim:

1. A method for determining the binding ability of a sample containing gabapentin comprising:

providing a vessel containing calcium channel subunits of 34893 2L cell line deposited under the Budapest Treaty as ATCC No. CRL-12108;

introducing into the vessel the sample containing gabapentin; and determining the binding ability of gabapentin to the cells.

* * * * *